US00PP20841P3

(12) United States Plant Patent

Pititto et al.

(10) Patent No.: US PP20,841 P3

(45) Date of Patent: Mar. 16, 2010

(54) RASPBERRY PLANT NAMED 'ERIKA'

(50) Latin Name: *Rubus idaeus L.*
Varietal Denomination: Erika

(75) Inventors: Antonio Pititto, Civezzano (IT); Luigi Gadler, Pergine Valsugana (IT); Flavio Roberto De Salvador, Marino (IT)

(73) Assignee: Centro Di Ricerca per La Frutticoltura, Rome (IT)

( * ) Notice: Subject to any disclaimer, the term of this patent is extended or adjusted under 35 U.S.C. 154(b) by 0 days.

(21) Appl. No.: 12/075,346

(22) Filed: Mar. 11, 2008

(65) Prior Publication Data

US 2009/0235415 P1 Sep. 17, 2009

(51) Int. Cl.
*A01H 5/00* (2006.01)

(52) U.S. Cl. ..... Plt./204

(58) Field of Classification Search ..... Plt./204
See application file for complete search history.

*Primary Examiner*—Kent L. Bell
(74) *Attorney, Agent, or Firm*—Medlen & Carroll, LLP

(57) ABSTRACT

A new Raspberry plant particularly distinguished by being a primocane raspberry plant having favourable fruit color and flavour, large and firm berry, and good tolerance to raspberry pests and diseases, is disclosed.

1 Drawing Sheet

Genus and species: *Rubus idaeus L.*
Variety denomination: 'Erika'.

BACKGROUND OF THE NEW PLANT

The present invention comprises a new and distinct cultivar of red raspberry, botanically known as *Rubus idaeus L.,* and hereinafter referred to by the cultivar name 'Erika'. 'Erika' was produced from an open pollination of the female parent 'Autumn Bliss' (U.S. Plant Pat. No. 6,597).

The new cultivar was created in 2002, in Trentino, Italy and has been asexually reproduced repeatedly by root cuttings since May 2007. The present invention has been found to retain its distinctive characteristics through successive asexual propagations in Trentino, Italy.

Plant breeder's rights were applied for with the European Union on Mar. 12, 2007. 'Erika' has not been made publicly available more than one year prior to filing of this application.

SUMMARY OF THE INVENTION

The following are the most outstanding and distinguishing characteristics of this new cultivar when grown under normal horticultural practices in Trentino, Italy.

a. Primocane raspberry plant;
b. Favorable fruit color and flavor;
c. Large and firm berry; and
d. Good tolerance to raspberry pests and diseases.

DESCRIPTION OF THE PHOTOGRAPHS

This new raspberry plant is illustrated by the accompanying photographs which show the fruit of the plant as well as the primocanes; the colors shown are as true as can be reasonably obtained by conventional photographic procedures. The photographs are of plants that are 2 years old.

Figure 1:
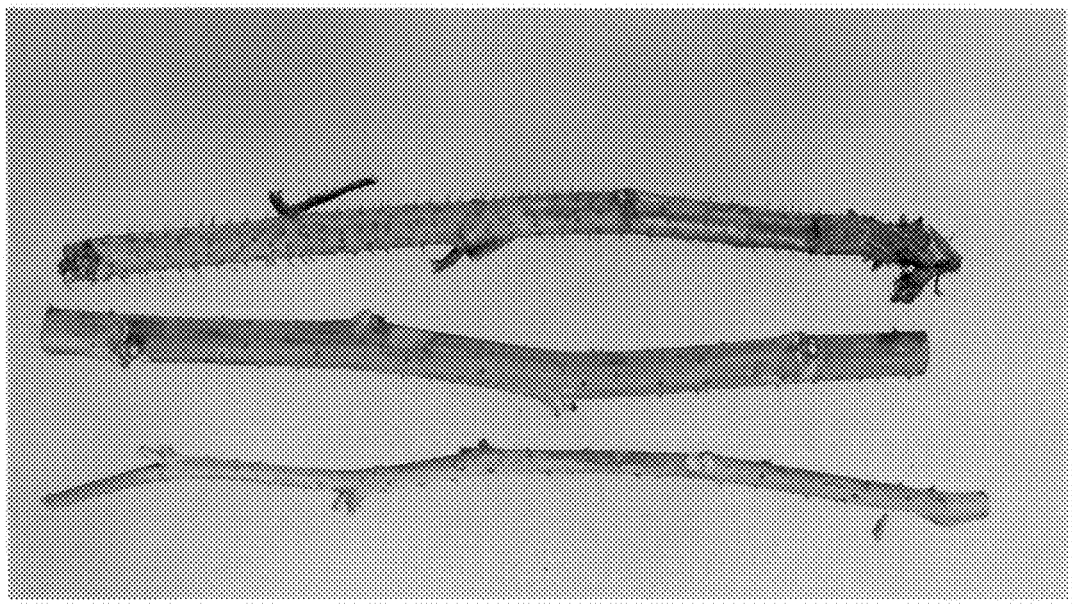
Figure 2:
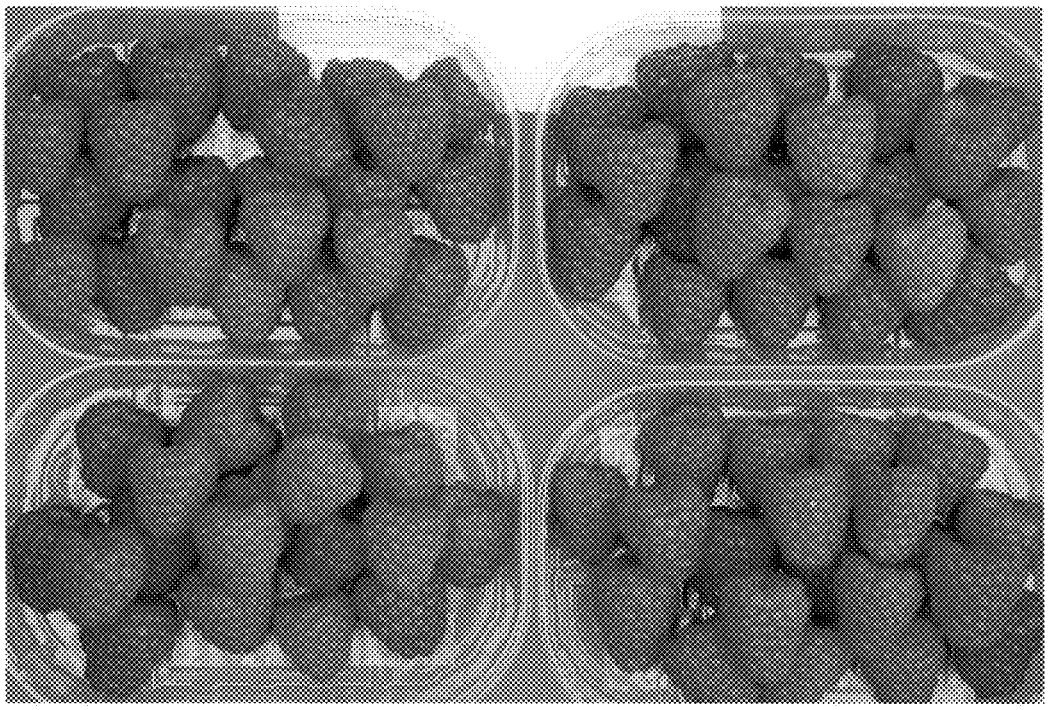

FIG. 1 shows sections of the canes.
FIG. 2 shows the mature fruit.

DESCRIPTION OF THE NEW CULTIVAR

The following detailed descriptions set forth the distinctive characteristics of 'Erika'. The data which define these characteristics were collected from root cuttings in Trentino, Italy. The plant history was taken on plants grown for 2 years under field conditions with natural light during the Autumn or primocane season. Color references are primarily to The R.H.S. Colour Chart of The Royal Horticultural Society of London (R.H.S.) (2001 edition).

DETAILED BOTANICAL DESCRIPTION

Classification:
- *Family.*—Rosaceae.
- *Botanical.*—*Rubus idaeus L.*
- *Common name.*—Raspberry.

Parentage: An open pollination of the female parent Raspberry plant 'Autumn Bliss' (U.S. Plant Pat. No. 6,597)

Plant:
- *Propagated.*—Root cuttings. Self-fertile.

Primocanes:
- *Cane color.*—RHS 144A (Yellow-green).
- *Spines.*—Present, thin and dense.
- *Length.*—1.8 m to 2.0 m.
- *Diameter.*—0.8 cm to 1.0 cm.
- *Texture.*—Smooth.
- *Internode length.*—4.0 cm to 5.0 cm.

Lateral branches:
- *Number of fruiting lateral branches per plant.*—8 to 10.
- *Length of the fruiting lateral branch.*—35.0 cm to 40.0 cm.
- *Diameter of the fruiting lateral branch.*—0.5 cm to 0.6 cm.
- *Texture of the fruiting lateral branch.*—Smooth.
- *Color of the fruiting lateral branch.*—RHS 142A (Green).

Spines:
- *Number (quantity)* of spines per specified linear shoot extension.—5 to 6 spines per cm.
- *Shape.*—Conical.
- *Length.*—Very short.
- *Width.*—Large at the base.
- *Apex.*—Hooked.
- *Color.*—RHS 183B (Greyed-purple).

Leaves:

*Type.*—Compound; 3 leaflets.

*Arrangement.*—Free.

*Leaf and leaflet length.*—10.5 cm to 11.0 cm.

*Leaf and leaflet width.*—7.0 cm to 7.5 cm.

*Leaf and leaflet shape.*—Straight.

*Leaf and leaflet color.*—Upper surface: RHS 147A (Yellow-green). Lower surface: RHS 145A (Yellow-green).

*Petiole.*—Length: 3.5 cm to 4.5 cm. Diameter: 0.25 cm to 0.30 cm. Color: RHS 143A (Green).

Stipules:

*Quantity per leaf.*—2.

*Shape.*—Erect.

*Length.*—0.45 cm to 0.55 cm.

*Width.*—Very narrow; 0.03 cm to 0.05 cm.

*Color* (*both surfaces*).—RHS 144A (Yellow-green).

Flowers:

*Height.*—0.65 cm to 0.75 cm.

*Diameter.*—0.8 cm to 1.0 cm.

*Bud.*—Shape: Elonged conical. Length: Medium. Diameter: Thin. Color: RHS 140A (Green).

*Petals.*—Number per flower: 6. Shape: Narrow elliptical. Length: 0.71 cm to 0.79 cm. Width: 0.35 cm to 0.38 cm. Apex: Rounded. Base: Very narrow. Margin: Smooth and regular. Texture: Smooth. Color (both surfaces): RHS 155C (White).

*Sepals.*—Number per flower: 6. Shape: Triangular. Length: 0.45 cm to 0.48 cm. Width: Broad at the base. Apex: Acuminate. Base: Large at the base forming the calyx. Margin: Smooth and regular. Texture: Smooth. Color (both surfaces): RHS 140A (Green).

*Blooming period of the plant* (*in cool areas*).—First bloom: July 10 through July 15. Full bloom: August 1 through August 10.

Fruit:

*Predominant shape.*—Broad-conical.

*Weight.*—4.85 g.

*Size.*—Length: 2.341 cm. Width: 2.176 cm.

*Color of mature fruit.*—RHS 53A (Red) and later on becoming RHS 59A (Red-purple).

*Firmness* (*Newtons/mm*).—2.18.

*Vigor.*—Medium.

*Harvest time* (*in cool areas*).—The first picking is September 10 through September 20; the last picking is October 25 through October 30.

*Time of ripening.*—First maturity is September 5 through September 10.

*Fruit grading* % (*percentage of fruit greater than* 22 *mm*).—10 to 20%.

*Production* (*kg/plant*).—20 to 30% higher yield than 'Polka'; 'Polka' has approximately a 2.5 kg/plant yield.

*Tritratable acidity* (*meq/l*).—25.58.

*Brix.*—6.27.

*Pedicel.*—Diameter: 0.15 cm to 0.22 cm. Color: RHS 145B.

*Number of druplets per fruit.*—100 to 110.

*Use/market.*—The berries are suitable for consumption as high grade fresh fruit and also are amenable to processing.

*Keeping quality.*—Fruit color is medium red but tends to become dark red in case of late harvest. Shelf life is good.

*Shipping quality.*—Good; attitude to conservation permits shipping.

Reproductive organs:

*Number of pistils per flower.*—35 to 45.

*Ovary.*—Shape: Pyriform. Length: Short. Width: Narrow. Color: RHS 142A (Green).

*Style.*—Length: 0.22 cm to 0.25 cm. Color: RHS 155C (White).

*Stamen.*—Number per flower: 50 to 60. Length: Very short. Shape: Double ovate. Color: RHS 183B (Greyed-purple).

*Pollen.*—Amount: Moderate. Color: RHS 145B (Yellow-green).

Disease and insect resistance: Good tolerance has been observed to typical raspberry pests and diseases.

COMPARISON WITH PARENTAL AND COMMERCIAL CULTIVARS

'Erika' differs from the female parental variety 'Autumn Bliss' (U.S. Plant Pat. No. 6,597) in that 'Erika' has a broad-conical shaped, light-red colored fruit weighing 4.85 g, while 'Autumn Bliss' has a oval-conical shaped, medium to dark-red colored fruit weighing between 3.5 g to 4.0 g.

'Erika' is similar to the commercial variety 'Polka' (unpatented), however, as shown in Table 1, there are numerous differences.

TABLE 1

Characteristic Comparison between 'Erika' and 'Polka'

| Characteristic | 'Erika' | 'Polka' |
|---|---|---|
| Plant vigor | Medium | Medium-high |
| Canes color | Yellow-green | Light-brown |
| Spines | Thin and dense | Thick and short |
| Fruit shape | Broad-conical | Conical |
| Ripening time | 8 days earlier than 'Polka' | Early (day 0) |
| Fruit color | Light-red | Red |

I claim:

1. A new and distinct cultivar of Raspberry plant as shown and described herein.

* * * * *